US00PP30070P2

(12) United States Plant Patent
Pineau

(10) Patent No.: US PP30,070 P2
(45) Date of Patent: Jan. 8, 2019

(54) ***HIBISCUS* PLANT NAMED 'MINDOUV5'**

(50) Latin Name: *Hibiscus syriacus*
Varietal Denomination: MINDOUV5

(71) Applicant: HORTIVAL DIFFUSION SAS, Beaufort-en-Anjou (FR)

(72) Inventor: Patrick Pineau, Saint Mathurin sur Loire (FR)

(73) Assignee: PEPINIERES MINIER SA, Beufort en Vallee (FR)

( * ) Notice: Subject to any disclaimer, the term of this patent is extended or adjusted under 35 U.S.C. 154(b) by 0 days.

(21) Appl. No.: 15/530,126

(22) Filed: Dec. 5, 2016

(51) Int. Cl.
*A01H 5/02* (2018.01)

(52) U.S. Cl.
USPC ..... Plt./257

(58) Field of Classification Search
USPC ..... Plt./257
See application file for complete search history.

*Primary Examiner* — Keith O. Robinson
(74) *Attorney, Agent, or Firm* — Penny J. Aguirre

(57) ABSTRACT

A new cultivar of *Hibiscus* named 'MINDOUV5', characterized by its large double flowers that are purple in color, its sterile flowers, its upright pant habit and its vigorous growth habit.

2 Drawing Sheets

Botanical classification: *Hibiscus syriacus*.
Cultivar designation: 'MINDOUV5'.

CROSS REFERENCE TO RELATED APPLICATIONS

This application is co-pending with a U.S. Plant Patent Application filed for a plant derived from the same breeding program entitled *Hibiscus* Plant Named 'MINDOUR1' (U.S. Plant patent application Ser. No. 15/530,127). This application is related to a European plant breeders' rights application filed on Jun. 2, 2014, application No. 2014/4162. There have been no offers for sale anywhere in the world more than one year prior to the filing of this Application and no accessibility to one of ordinary skill in the art could have been derived from the printed plant breeder's rights documents.

BACKGROUND OF THE INVENTION

The present invention relates to a new and distinct cultivar of *Hibiscus* plant, botanically known as *Hibiscus syriacus* 'MINDOUV5', and will be referred to hereafter by its cultivar name, 'MINDOUV5'. 'MINDOUV5' is a new cultivar of Rose of Sharon, a deciduous shrub grown for use as a landscape plant.

The new cultivar of *Hibiscus* arose from a breeding program conducted by the Inventor in La Menitre, France in 2007. 'MINDOUV5' originated as a seedling that arose from seed planted from open pollination of a plant of *Hibiscus syriacus* from the Inventor's breeding program, reference no. 3436, as the female parent (not patented). The male parent is unknown. 'MINDOUV5' was selected as a single unique plant in 2011 from the resulting seedlings from the above cross.

Asexual propagation of the new cultivar was first accomplished by grafting in La Menitre, France in 2012 by the Inventor. Asexual propagation by grafting and stem cuttings has determined that the characteristics of the new cultivar are stable and are reproduced true to type in successive generations.

SUMMARY OF THE INVENTION

The following traits have been repeatedly observed and represent the characteristics 'MINDOUV5'. These attributes in combination distinguish 'MINDOUV5' as a new and distinct cultivar of *Hibiscus*.

1. 'MINDOUV5' exhibits large double flowers that are purple in color.
2. 'MINDOUV5' exhibits sterile flowers.
3. 'MINDOUV5' exhibits an upright pant habit.
4. 'MINDOUV5' exhibits a vigorous growth habit.

The female parent plant, No. 3436, differs from 'MINDOUV5' in having flowers that are red-purple in color, are less double and fertile. 'MINDOUV5' can be most closely compared to *Hibiscus syriacus* 'Ardens' (not patented) and 'MINDOUR1'. 'Ardens' is similar to 'MINDOUV5' in having flowers that are purple in color. 'Ardens' differs from 'MINDOUV5' in having a less vigorous growth habit and flowers that are smaller in size and less double. 'MINDOUR1' is similar to 'MINDOUV5' in have large double and sterile flowers and in having a vigorous growth habit. 'MINDOUR1' differs from 'MINDOUV5' in having flowers that are red-purple in color.

BRIEF DESCRIPTION OF THE DRAWINGS

The accompanying colored photographs illustrates the overall appearance and distinct characteristics of the new *Hibiscus*. The photographs were taken of plants 4 years in age as grown outdoors in Menitre, France.

The photograph in FIG. 1 provides a side view of 'MINDOUV5' in bloom.

Figure 1:
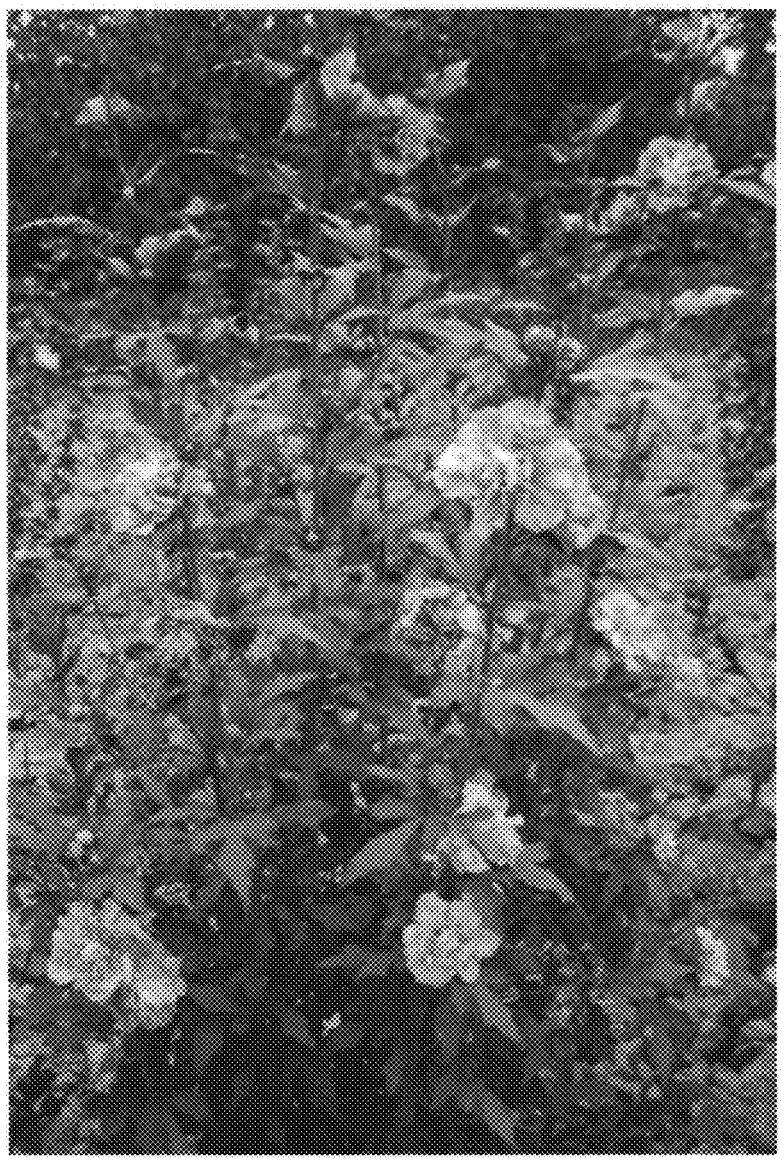
Figure 2:
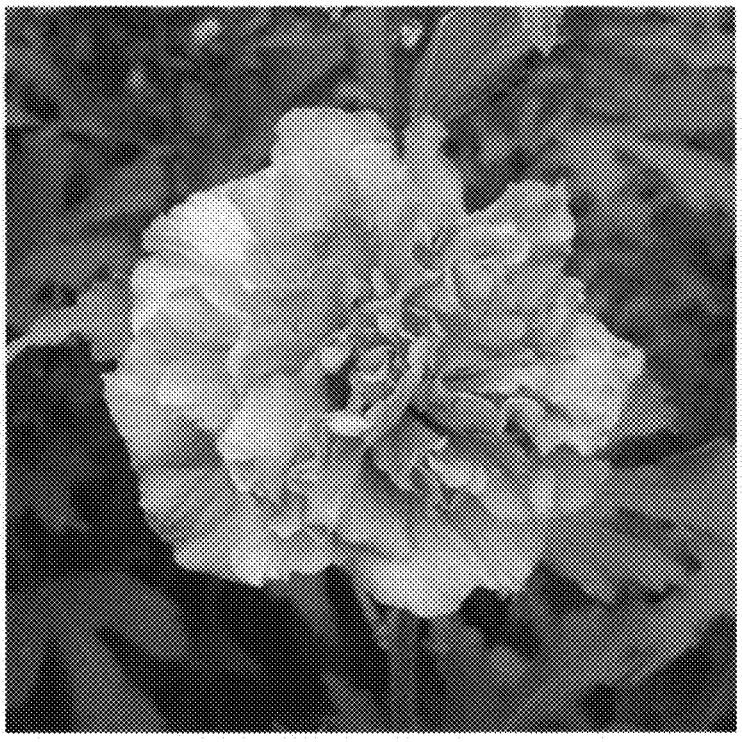

The photograph in FIG. 2 provides a close-up view of the flower and of 'MINDOUV5'.

Figure 3:
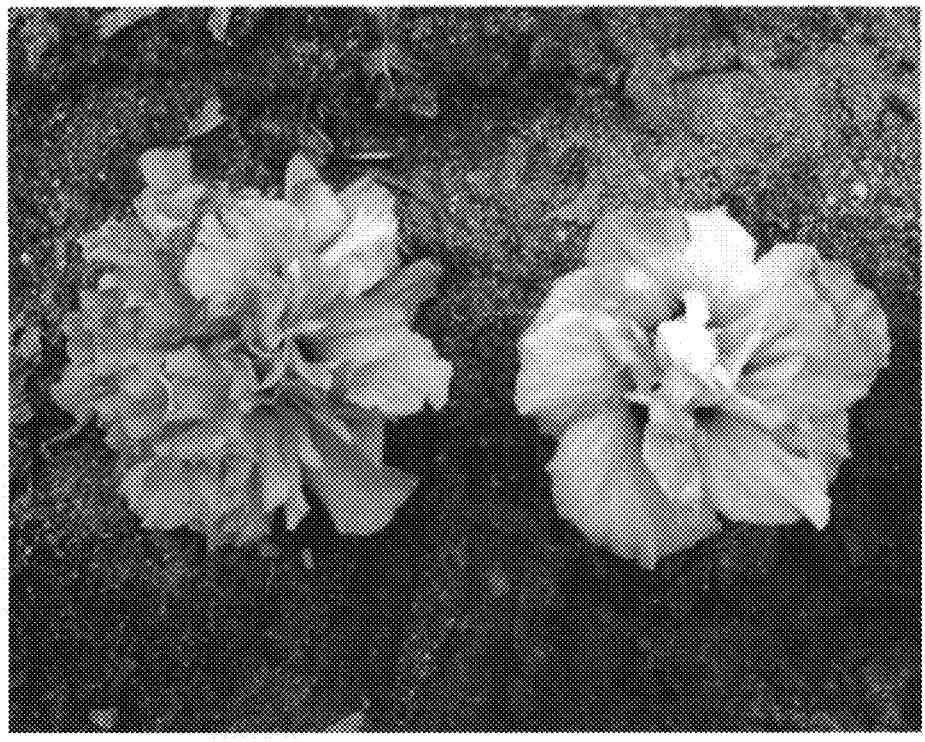

The photograph in FIG. 3 provides a comparison between a flower of 'MINDOUV5' on the left and a flower of 'Ardens' on the right.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 4 year-old plants of the new cultivar as grown in two-gallon containers in a greenhouse and outdoors in St Paul, Minn. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period.*—8 weeks from mid summer to early fall in La Menitre, France.

*Plant type.*—Deciduous shrub.

*Plant habit.*—Upright.

*Height and spread.*—Reaches 1.6 m in height and 70 cm in spread as a 4 year-old plant in the landscape.

*Hardiness.*—At least to U.S.D.A. Zone 4.

*Diseases.*—No susceptibility or resistance to diseases has been observed.

*Root description.*—Fleshy roots (4 mm in diameter), a blend of 138B and 159A in color, fibrous roots from fleshy roots; 164D in color.

*Root development.*—About 33 days to produce a young rooted plant from a graft.

*Propagation.*—Grafting.

*Growth rate.*—Vigorous.

Stem description:

*Shape.*—Slightly oval to round.

*Stem color.*—New growth; a blend 143A lateral and secondary stems, mature wood; a blend of 202B to 202C and 201B, with striations and lenticels of 159.

*Stem size.*—Main stem; an average of 18 cm in length and 3 cm in width, lateral stems; an average of 30 cm in length and 1 cm in diameter, secondary stems; an average of 45 cm in length and 4 mm in width.

*Stem surface.*—New growth; pubescent, maturing wood; relatively smooth with striations.

*Stem aspect.*—Held upright with secondary stems held about 15° to vertical.

*Stem strength.*—Very strong.

*Branching.*—An average of 1 main stem, 7 lateral stems, and 2 to 3 secondary stems per lateral branch.

*Internode.*—Average of 1.5 cm.

*Lenticels.*—159A in color, an average of 30 per stem section that is 3 cm in length and 1 cm in width, roughly orbicular in shape, 2 mm in diameter.

Foliage description:

*Leaf shape.*—Ovate to broadly lanceolate overall.

*Leaf division.*—Simple or 3-leaved.

*Leaf base.*—Cuneate.

*Leaf apex.*—Acute.

*Leaf venation.*—Pinnate, color matches leaf coloration.

*Leaf margins.*—Tri-lobed, deeply lobed, upper part of all lobes are serrate to crenate with lower part entire.

*Leaf attachment.*—Petiolate.

*Leaf arrangement.*—Alternate.

*Leaf orientation.*—Held downward to vertical.

*Leaf aspect.*—Slightly cupped inward to flat.

*Leaf surface.*—Very finely puberulent on upper and lower surface (appears glabrous).

*Leaf color.*—Young and mature leaves; upper surface and lower surface 146A, variegation absent.

*Leaf size.*—Average of 7.5 cm in length and 5 cm in width when 3-leaved and an average of 7 cm in length and 3 cm in width when simple.

*Leaf quantity.*—Average of 36 leaves per lateral branch 30 cm in length.

*Petioles.*—Average of 1.5 cm in length and 3 mm in diameter, 137B in color, pubescent surface.

*Stipule.*—2 at the base of each petiole, 5 mm in length, 1 mm in width, round in shape, pointed apex, glabrous surface, 146A in color.

Flower description:

*Inflorescence type.*—Fully double flowers in clusters of 3 to 4 at terminus.

*Inflorescence size.*—With one flower open and 2 buds an average of 11 cm in width and 8 cm in height.

*Lastingness of flowers.*—About 5 days, self cleaning.

*Flower size.*—An average of 4 cm in depth and 9 cm in diameter.

*Flower fragrance.*—Very faint rose scent.

*Flower shape.*—Carnation-like.

*Flower number.*—5 per lateral stem.

*Flower aspect.*—Upright to slightly outward.

*Flower bud.*—Elliptic-globose in shape, an average of 1 cm in length and 8 mm width, 145A in color.

*Flower attachment.*—Peduncle.

*Petal and petaloid number.*—Average of 5 petals and 25 petaloid stamens.

*Petal and petaloid shape.*—Petals; orbicular to broadly oblanceolate to elliptic, petaloid stamen; range from oblong to elliptic to oblanceolate.

*Petal and petaloid stamen color.*—Upper and lower surface when newly opening; a blend of 83A and N81A, margins N77A, veins 85D, upper surface when fully open; a blend of N82B, 84A and 84B and 84C, mid section to tip a blend of N82B and 84A, as it matures, turning to a blend of 92A to 92C and 94A, tips 92C, eye zone; small in size, center and base of eye zone 53A, eye zone extensions about 2 mm in length blush out to become NN78A, some have vein coloration of N155B, lower surface when fully open; a blend of N82B, 84A and 84B and 84C, mid section to tip a blend of N82B and 84A, as it matures, turning to a blend of 92A to 92C and 94A, tips 92C, base a blend of NN155B and 84B, base spot NN78A, vein coloration of N155B.

*Petal and petaloid stamen surface.*—Both surfaces smooth and dull, center petals are glossy.

*Petal attitude.*—Outer most petals are moderately ascending.

*Petal and petaloid stamen margins.*—Medium undulation and curled under.

*Petal and petaloid stamen apex.*—Rounded to wavy to notched.

*Petal and petaloid stamen base.*—Cuneate.

*Petal and petaloid stamen size.*—Petals; up to 4 cm in length and 3 cm in width, petaloid stamens; range from 4 cm in length and 1.5 cm in width to 2 cm in length and 1 cm in width.

*Sepal number.*—5.

*Sepal shape.*—Triangular.

*Sepal margin.*—Entire.

*Sepal size.*—Average of 1 cm in length and 5 mm in width, free portion is triangular in shape and 6 mm in length.

*Sepal aspect.*—Upright.

*Sepal surface.*—Outer surface puberulent, inner surface glabrous and glossy.

*Sepal apex.*—Apiculate.

*Sepal base.*—60% of base is fused.

*Sepal color.*—Young and mature outer and inner surface; 141A to 141C.

*Calyx.*—Campanulate in shape, average of 4 mm in depth and diameter.

*Peduncles.*—An average of 5 cm in length and 2 mm in diameter, strong and stout, held upright to outward from stem, 138A in color, pubescent surface.

*Pedicels.*—Not present, flowers are solitary from peduncles attached to terminus.

*Bracts.*—6 to 8 bracts held close to calyx, linear in shape, apiculate apex, truncate base, entire margins, average of 1.4 cm in length and 1 mm in width, inner and outer surface a blend of 139A and 141D in color, inner surface is smooth, outer surface is pubescent.

Reproductive organs:

*Gynoecium.*—5 pistils, 1 cm in length, stigmas; 142C in color, puberulent surface, club shaped, and 2 mm in diameter, style; 142C in color and 8 mm in length, ovary; urn-shaped, 9 mm in length and 6 mm in width, 142C in color, pollen is moderate and NN155C in color.

*Androecium.*—Stamens; some remain attached to the margins of the petaloid stamens in the center of the flower, average of 10, anther; 1 mm in diameter, flattened in shape, 145D in color, some filaments observed extending below the petaloid stamen an average of 4, NN155C, 3 mm in length, smooth surface.

*Fruit/seeds.*—None produced.

It is claimed:

1. A new and distinct cultivar of *Hibiscus* plant named 'MINDOUV5' as herein illustrated and described.

* * * * *